United States Patent
Gramann et al.

(10) Patent No.: US 10,231,810 B2
(45) Date of Patent: Mar. 19, 2019

(54) DENTAL IRRADIATION DEVICE AND SYSTEM

(71) Applicant: 3M INNOVATIVE PROPERTIES COMPANY, Saint Paul, MN (US)

(72) Inventors: Jens Gramann, Gräfelfing (DE); Stefan K. Welke, Seefeld (DE); Thomas Müeller, Seefeld (DE); Korbinian Schepke-Gerlach, Seefeld (DE); Ralf Kelz, Seefeld (DE); Karin Watzek, Seefeld (DE); Manfred Harre, Seefeld (DE); Rudolf Schmid, Seefeld (DE)

(73) Assignee: 3M Innovative Properties Company, St. Paul, MN (US)

( * ) Notice: Subject to any disclaimer, the term of this patent is extended or adjusted under 35 U.S.C. 154(b) by 833 days.

(21) Appl. No.: 14/427,699

(22) PCT Filed: Sep. 13, 2013

(86) PCT No.: PCT/US2013/059686
§ 371 (c)(1),
(2) Date: Mar. 12, 2015

(87) PCT Pub. No.: WO2014/043488
PCT Pub. Date: Mar. 20, 2014

(65) Prior Publication Data
US 2015/0250572 A1    Sep. 10, 2015

(30) Foreign Application Priority Data

Sep. 14, 2012 (EP) .................................... 12184443

(51) Int. Cl.
*A61C 13/15* (2006.01)
*A61B 1/06* (2006.01)
(Continued)

(52) U.S. Cl.
CPC .............. *A61C 19/004* (2013.01); *A61B 1/05* (2013.01); *A61B 1/06* (2013.01); *A61B 1/0676* (2013.01);
(Continued)

(58) Field of Classification Search
CPC ....... A61C 19/004; A61C 19/003; A61B 1/05; A61B 1/051; A61B 1/0053; A61B 1/0638; A61B 1/06; A61B 1/0676; A61B 1/0684
See application file for complete search history.

(56) References Cited

U.S. PATENT DOCUMENTS 4,608,622 A * 8/1986 Gonser ................ A61C 19/003
250/493.1
5,147,204 A    9/1992 Patten
(Continued)

FOREIGN PATENT DOCUMENTS

CN     201481570     5/2010
EP     2078493       7/2009
(Continued)

OTHER PUBLICATIONS

International Search report for PCT International Application No. PCT/US2013/059686 dated Dec. 5, 2013, 4 pages.

*Primary Examiner* — Nicholas Lucchesi
*Assistant Examiner* — Shannel Wright

(57) ABSTRACT

A dental irradiation device comprises a first light emitting unit for emitting blue light adapted for light hardening of a dental material. The device further comprises a second light emitting unit and an image sensing unit which are adapted for cooperation with each other for simultaneous illumination and image capturing. The device facilitates hardening of dental materials and provides, inter alia, additional diagnostic functions.

15 Claims, 6 Drawing Sheets

(51) Int. Cl.
  *A61B 1/247* (2006.01)
  *A61B 1/05* (2006.01)
  *A61B 1/24* (2006.01)

(52) U.S. Cl.
  CPC .............. *A61B 1/0684* (2013.01); *A61B 1/24* (2013.01); *A61B 1/247* (2013.01); *A61B 1/0653* (2013.01); *F04C 2270/041* (2013.01)

(56) References Cited

U.S. PATENT DOCUMENTS

| | | | |
|---|---|---|---|
| 5,290,169 A | 3/1994 | Friedman | |
| 5,737,013 A * | 4/1998 | Williams | A61B 1/00177 348/66 |
| 6,254,385 B1 | 7/2001 | Jung | |
| 6,271,913 B1 | 8/2001 | Jung | |
| 6,276,934 B1 | 8/2001 | Rakocz | |
| 6,384,917 B1 * | 5/2002 | Fradkin | G01J 3/02 356/402 |
| 6,500,001 B2 | 12/2002 | Horth | |
| 6,531,802 B2 | 3/2003 | Umeda | |
| 6,611,110 B1 * | 8/2003 | Fregoso | A61C 19/004 315/224 |
| 6,631,829 B1 | 10/2003 | Wagner | |
| 6,695,614 B2 | 2/2004 | Plank | |
| 6,724,522 B2 | 4/2004 | Hartung | |
| 6,976,841 B1 * | 12/2005 | Osterwalder | A61C 9/0006 433/29 |
| 2002/0007177 A1 * | 1/2002 | Campin | A61F 9/008 606/5 |
| 2003/0011768 A1 * | 1/2003 | Jung | A61B 5/0088 356/326 |
| 2003/0147258 A1 | 8/2003 | Fischer | |
| 2003/0228553 A1 * | 12/2003 | Mandelkern | A61B 1/00016 433/29 |
| 2004/0201980 A1 | 10/2004 | Fischer | |
| 2004/0218039 A1 * | 11/2004 | Cooper | A61B 1/05 348/66 |
| 2004/0248059 A1 | 12/2004 | Katsuda | |
| 2005/0003323 A1 * | 1/2005 | Katsuda | A61B 1/00089 433/29 |
| 2006/0173358 A1 * | 8/2006 | Xie | A61B 1/00009 600/476 |
| 2006/0245187 A1 * | 11/2006 | Scott | A61C 19/004 362/231 |
| 2008/0017787 A1 * | 1/2008 | Okawa | A61B 1/0615 250/226 |
| 2009/0208894 A1 * | 8/2009 | Orloff | A61C 19/004 433/29 |
| 2010/0003633 A1 * | 1/2010 | Senn | A61C 19/004 433/29 |
| 2010/0190130 A1 * | 7/2010 | LaRocque | A61C 19/004 433/29 |
| 2010/0238279 A1 * | 9/2010 | Thoms | A61B 1/00089 348/77 |
| 2010/0253773 A1 * | 10/2010 | Oota | A61B 1/24 348/77 |
| 2013/0023966 A1 * | 1/2013 | Depfenhart | A61B 18/203 607/89 |
| 2013/0141558 A1 * | 6/2013 | Jeon | A61B 1/00177 348/77 |
| 2013/0330684 A1 * | 12/2013 | Dillon | A61B 1/00039 433/29 |
| 2013/0344456 A1 * | 12/2013 | Jessop | A61C 19/004 433/29 |
| 2014/0051040 A1 * | 2/2014 | Kilcher | A61C 19/004 433/226 |
| 2014/0078507 A1 * | 3/2014 | Labrie | A61C 19/003 356/446 |
| 2016/0074144 A1 * | 3/2016 | Peterson | A61C 19/004 433/29 |

FOREIGN PATENT DOCUMENTS

| | | |
|---|---|---|
| JP | 2008-086554 | 4/2008 |
| WO | WO 2005-104926 | 11/2005 |
| WO | 2007-054692 | 5/2007 |

* cited by examiner

DENTAL IRRADIATION DEVICE AND SYSTEM

FIELD OF THE INVENTION

The invention relates to a dental irradiation device which is adapted for emitting blue light for light hardening of a dental material as well as for image capturing including lighting for the image capturing. Further the invention relates to a system comprising such a device and a computer connectable with the device.

BACKGROUND ART

Light hardenable or light curable materials are widely used in dentistry for the restoration of teeth. Many of such materials are made to provide optical characteristics that resemble those of natural teeth. Further such materials typically can be placed precisely and conveniently, can be hardened instantly, and the hardened material is typically relatively durable. Accordingly these materials are favored alternatives to less pleasant looking and over time self-hardening materials, like for example amalgam.

Light hardenable materials often include a polymerizable matrix material and filler materials including colorants, and may initially be generally soft or flowable so that they can be applied in a desired location and shape. For example, for restoration of a tooth the dental material may be filled into a tooth cavity and shaped so that the restored tooth resembles a natural tooth. Once the desired shape has been formed, the material may be cured by exposing it to light of a desired wavelength. The light typically activates photoinitiators in the dental material that cause the matrix material to polymerize.

The use of dental materials that are hardenable by blue light of a wavelength of between about 450 and 500 nm (nanometers) has become common in dentistry. Accordingly, light-emitting devices used for hardening such dental materials typically emit light at such wavelengths. Such a light-emitting device is for example available from 3M Deutschland GmbH, Germany, under the trade designation Elipar™ S10.

A variety of light devices have been developed or proposed. For example U.S. Pat. No. 5,147,204 discloses a light emitting apparatus for curing photocurable dental materials. The apparatus includes a handpiece having a housing, a depending handle and a detachable light guide. The light guide is received in a head connected to the housing. Rotational movement of the head relative to the housing also rotatably moves the light guide so that the guide may be turned by the same hand of the user that is grasping the handle. Additionally, a pivotal connection between the housing and the handle permits limited pivotal adjustment of the angle of the housing relative to the handle for improved manipulation and user comfort.

Because appropriate powerful, small and inexpensive light emitting diodes (LEDs) have become available over the past years, in some dental light hardening devices the light source has been placed directly in the intra-oral tip portion so that an elongated light guide for guiding light from the handle into the intra-oral tip could be eliminated.

For example US 2003/0147258 discloses a light curing device which includes a light source disposed at a distal end and a focusing means configured to focus light emitted from the light source. The light source is an LED light source and may include any quantity of LEDs. The focusing means includes lenses configured to collimate the light emitted from the light source.

Although there are a variety of light devices on the market there is still a desire to provide a device that is relatively convenient in handling. Further such a device is desirably inexpensive. There is also a desire to provide a device which can be used at a relatively high level of hygiene.

SUMMARY OF THE INVENTION

In one aspect the invention relates to a dental irradiation device which comprises a first light emitting unit for emitting blue light. The blue light is adapted for light hardening of a dental material. The dental irradiation device further comprises a second light emitting unit and an image sensing unit. The second light emitting unit and the image sensing unit are adapted for cooperation with each other for simultaneous illumination and image capturing.

The invention is advantageous in that it preferably facilitates the positioning of the device relative to a patient's tooth, for example a tooth to be restored. Thereby the invention preferably helps minimizing the risk of imperfectly hardened dental material (for example filling material) due to incorrect positioning of the blue light relative to the dental material placed to the tooth or placed in a cavity of the tooth. Further the invention may support and facilitate an appropriate selection of the color of the dental material relative to a tooth to be restored. The invention is thus advantageous in that it may help maximizing the quality of a dental treatment, for example a dental filling. Further the invention is advantageous in that it provides for additional diagnostic functions, for example without the need of additional devices. The invention may further help maximizing the safety for patients and users during hardening of dental materials by relative intense blue light. Further the invention may help minimizing the time for a dental treatment, and thus may help minimizing costs.

For the purpose of the present specification the term "blue light" refers to light having a wavelength within the range of about 430 nm to 500 nm, preferably within a range of about 430 nm to 480 nm.

In one embodiment the first light emitting unit, the second light emitting unit and the image sensing unit are simultaneously present in the device. Nevertheless the first light emitting unit, the second light emitting unit and the image sensing unit may be independently activatable and deactivatable by electric control.

In one embodiment the image sensing unit is adapted for image capturing of a reference area at a reference position of the device relative to the reference area. The first light emitting unit may be arranged in the device for irradiation of the reference area in the same reference position of the device. Accordingly a user may position the device by monitoring the actual position of the device relative to the reference area (for example a tooth prepared with a still unhardened dental material in a tooth cavity). Once the device is appropriately positioned the user may activate the first light emitting unit for hardening the dental material without change of the position of the device.

In a further embodiment the device may comprise a positioning aid. The positioning aid may comprise a laser pointer for projecting a point toward the reference area. Further the positioning aid may comprise a crosshair which may be displayed relative to the image captured by the image sensing unit. Thus a user may position the device by help of the positioning aid such that the center of the blue light beam is positioned to a particular position indicated by the laser point or crosshair. Accordingly the blue light may be directed with its area of highest intensity toward the desired position.

In a further embodiment the second light emitting unit is arranged in the device for illumination of the reference area in the same reference position of the device. Accordingly in the same position of the device the reference area may be exposed to blue and white light and an image therefrom may be captured. The irradiation of the reference area by blue light may be performed alternatively to the illumination by white light and image capturing. Thus the image sensing unit may not need to operate under blue light conditions. Therefore an image conversion and/or light protection for the image sensing unit may not be necessary. Further the second light emitting unit is preferably adapted to emit white light. Thus the image sensing unit may be provided by standard components which often operate at white light conditions. This may help minimizing costs for making the device.

For the purpose of the present specification the term "white light" refers to light having a wavelength within a range of about 380 nm to 780 nm. Although white light may also comprise light at wavelengths overlapping with the range of wavelengths of blue light, the white light preferably does not predominantly consist of light within that range but has significant portions of visible light at wavelengths outside that range. In contrast the blue light preferably predominantly consists of light within a range of about 430 nm to 480 nm. The blue light may particularly not comprise light having a wavelength outside the range of about 430 nm to 480 nm at a substantial intensity or at all. In particular blue light may have a first portion of light within a range of about 430 nm to 480 nm and preferably does not have a significant second light portion within a range of 570 nm and 590 nm, wherein the maximum intensity of the second portion of light is preferably less than 10% and more preferably less than 1% of the maximum intensity of the first portion of light. Further blue light may not have a significant third light portion within the spectrum of visible light outside the range of 430 nm and 480 nm and outside the range of 570 nm to 590 nm, wherein the maximum intensity of any third portion of light is preferably less than 25% and more preferably less than 20% of the maximum intensity of the first portion of light.

In one embodiment the first light emitting unit has a first light output, the second light emitting unit has a second light output, and the image sensing unit has an image input. The first and second light output and the image input may be arranged in the device adjacent each other. For example the first and second light output and the image input may be jointly accommodated in a head at a free end of an intra-oral tip of the device. Therefore means for conveying light within the device may not be necessary. However in an alternative embodiment the image sensing unit may comprise an image sensor and an optical unit for guiding light between the image sensor and the image input. Although such an embodiment comprises means (the optical unit) for conveying light within the device such an embodiment may allow for using a larger image sensor for capturing images at a higher resolution, for example.

Further the first and the second light emitting unit each may comprise a light source adjacent the respective light output or a light guide arranged between the light source and the respective light output.

In a further embodiment the second light emitting unit is arranged in the device for emitting light in a first direction and the image sensor is adapted for image capturing from a second direction generally transverse to the first direction. The image sensing unit may comprise a light deflector for guiding light from the first direction toward the second direction.

In one embodiment each of the first and second light emitting unit comprises one or more light emitting diodes (LEDs). The image sensing unit preferably comprises a charge-coupled device (CCD) or a complementary metal-oxide-semiconductor (CMOS). The light emitting diodes (LEDs), and the image sensing unit may be provided on a chip-on-board (COB) module. The first light emitting unit may be formed of a single LED which is configured to emit light at a peak wavelength within a range of about 444 nm to about 452 nm. Further the second light emitting unit may comprise one or more LEDs having a semiconductor LED configured to emit light within a spectrum of blue of ultraviolet light and additionally a fluorescent material (for example a phosphor) which is adapted and arranged to convert the light emitted from the LED into white light. Although the term LED refers to "Light Emitting Diode" only, the combination of the LED including the fluorescent material is also referred to in short as "white LED" or "LED" herein.

In a further embodiment the dental irradiation device comprises a collimation optic for collimating light emitted from the first and/or second light emitting unit. Such a collimation optic may be selected from among a TIR lens™ (Total Internal Reflection lens) and a plano-convex lens. Further the dental irradiation device, in particular the image sensing unit, may comprise a fixed or variable optical zoom lens. A fixed optical zoom lens may comprise one or more optical lenses which provide for optical magnification, whereas a variable optical zoom lens may comprise three optical lenses of which at least one is movable relative to one of the other lenses.

In a further embodiment the dental irradiation device comprises a light wave converter for the first light emitting unit. Such a light wave converter may provide light at a light temperature of about 5000 K or greater (cool white). Thus the relatively intense blue light may be converted into relatively intense white light. Such white light may be used for trans-illumination of teeth, for example for diagnosis of caries. Substances for converting light in the visible range generally comprise substances that can luminesce, in particular fluoresce, when optically excited. A light wave converter as it may be used with the present invention is for example disclosed in U.S. Pat. No. 6,724,522. The device may have detachably attachable light guide, for example a light guide comprising one or more optical fibers. The light guide may comprise a collimation lens and optionally the light wave converter 115. Thus the converted light may be focused and guided toward and end of the light guide which may be placed toward a tooth to be trans-illuminated.

In one embodiment the dental irradiation device comprising a wireless data interface for transmitting image data obtained from the image sensing unit. The person skilled in the art is aware of a variety of wireless data interfaces according to for example IEEE 802.11, Bluetooth® or any other suitable proprietary or non-proprietary standard.

The dental irradiation device of the invention may generally comprise a body and an intra-oral tip. The body may be adapted to form a handle for a user. Further the body may comprise the electric circuitry and battery for controlling and powering the device, respectively. The device may be adapted for emitting light from the first and/or the second light emitting unit via the intra-oral tip. Further the device may be adapted for image capturing via the intra-oral tip.

Thus the optical interface comprising the first and second light output as well as the image input may be jointly accommodated in the intra-oral tip of the device (preferably in the head of the intra-oral tip at a free end thereof).

In a further embodiment the intra-oral tip and the body are rotatably interconnected with each other. Thus the light outputs and/or image input may be rotatable relative to the body of the device. A device, for example one that has an operation button at the body, may be conveniently held in the same position in different rotational positions of the intra-oral tip. The intra-oral tip and the body may be detachably interconnected with each other. Accordingly the intra-oral tip may be exchangeable or removable for cleaning and/or disinfecting.

In one embodiment at least the body of the device is hermetically encapsulated. The body preferably does not comprise any openings for connecting an inside of the body and the exterior of the device. In particular the body may not have any venting openings. This allows disinfection of the device without penetration of any disinfectant into the body. Thus disinfectant cannot reach electronic circuitry in the body. Accordingly thus the lifetime of the device may be maximized.

In a further aspect the invention relates to a dental irradiation system. The system comprises a dental irradiation device of the invention and a computer. The computer is preferably separate from the device (in particular is preferably not included within the dental irradiation device). The computer further is preferably connectable or connected to a computer screen. Further the computer is preferably adapted to receive image data from the dental irradiation device and to display an image based on the image data. The computer preferably has a wireless data interface for cooperation with the wireless data interface one or more of the dental irradiation units of the invention.

In one embodiment the computer is adapted for measuring a tooth color based on the image data. For example the CCD- or CMOS chip may provide image data in the form of different color data and the computer may have software for calculating a tooth color based thereon. The computer may be adapted to propose to a user a tooth color of a dental material which matches best the calculated tooth color. The user may select a dental material based on the proposal. It is noted that the tooth colors of actual teeth in a patient's mouth are within a continuous scale of tooth colors, whereas the tooth colors of dental material are typically standardized colors selected from a palette of discrete tooth colors. Hence a perfect match of the actual tooth color and the color of the dental material is typically not possible, and it has been found that matching of slightly different colors is difficult for many users. Therefore the invention may help maximizing the aesthetic appearance of the restored tooth by assisting in the selection of the dental material relative to the tooth color.

Further the computer may be adapted for determining a tooth color based on an interpretation of an encoding conveyed in the image data. For example the system may be adapted such that a bar code can be captured by the image sensing unit of the device, and the computer may have software for recognizing a (two or three-dimensional) bar code. The computer may further be adapted to retrieve a tooth color based on the recognized bar code.

In one embodiment the dental irradiation device is adapted to recognize the distance between the device and an object and to perform one or both of:
automatically adjusting the light intensity of the first light emitting unit depending on the determined distance; and/or
automatically setting a time period and automatically switching off the first light emitting unit upon lapse of this time period depending on the determined distance.

In a further embodiment the dental irradiation device is adapted to provide a signal to a user of the device depending on the distance between the device and the object. For example the device may provide a signal in case the device is out of range (for example too close to or too far away from the object). The signal may be one of an audible, visible and/or tactile (vibration) signal.

In an embodiment the image sensing unit of the dental irradiation device comprises an autofocus camera. The autofocus is preferably based on an autofocus mechanism which is adapted to physically move one or more lenses relative to a camera circuit (CCD or CMOS circuit). The autofocus is further preferably based on a wire made of a shape-memory alloy. The wire is preferably adapted to change in length if supplied with electric power. The autofocus mechanism further comprises a spring arranged in cooperation with the wire to act toward resetting any change of the wire in length.

The image sensing unit may be adapted to automatically focus to an object to be imaged, for example based on contrast detection. Preferably the dental irradiation device is further adapted to automatically focus to an object to be imaged and thereby (for example based on an electric or data output related to a position of any lenses in the autofocus camera) to recognize the distance of the object focused by the camera and to automatically adjust the light intensity of the first light emitting unit depending on the determined distance. Any distance of the object may be determined for example from the magnitude of the power supplied to the wire in the autofocus. Accordingly the dental irradiation device is preferably adapted to irradiate an object, for example a hardenable dental material, at generally uniform intensity independent from the distance (within a certain range of different distances) between the dental irradiation device and the object. Instead or in addition to an adjustment of the light intensity the device may be adapted to automatically set a time period and automatically switching off the first light emitting unit upon lapse of this time period depending on the determined distance.

In a further embodiment the device is adapted to recognize an image of a light spot on an object. The light spot is preferably projected to the object by the first and/or second light emitting unit (or by a further light source, for example a laser). The device is preferably further adapted to evaluate the size of the light spot and/or an area in which a predetermined minimum light intensity is recognized (for example from evaluating the brightness of the spot at different points). The device of this embodiment is preferably further adapted to automatically adjust the light intensity of the first light emitting unit depending on the image recognition of the light spot on the object. For example a smaller size of the light spot on the object may cause the device to lower the light intensity of the first light emitting unit relative to a larger size of the same light spot on the same object. Instead or in addition to an adjustment of the light intensity the device may be adapted to automatically set a time period and automatically switching off the first light emitting unit upon lapse of this time period depending on the image recognition of the light spot on the object.

In one embodiment the spot has a predetermined pattern, for example a cross, a square or a circle. Such a pattern may be generated by a lens and or an aperture arranged between the first and/or second light emitting unit and the object.

In a further embodiment the dental irradiation device has a color sensor in addition to the image sensing unit. Thus the dental irradiation device may be adapted to recognize a shape of an object independently from recognizing the same object's color. Therefore the accuracy of shape capturing as well as of color capturing may be maximized. The color sensor may comprise a CCD or CMOS camera circuit, but preferably has different and/or more color filters that the camera circuit of the image sensing unit. In particular the color sensor may comprise a plurality of light filters assigned to individual intensity sensors of the CCD or CMOS circuit. The color sensor may comprise more than three different color filters. In a preferred embodiment the color sensor is configured for measuring at least eight, preferably at least fifteen different colors. Therefore the color sensor may comprise at least eight or at least fifteen, thirty or even sixty different color filters. Each of the color filters may have a passband width within a range of 5 nm to 40 nm, more preferably within a range of 5 nm to 25 nm, most preferably within a range of 5 nm to 10 nm.

In one embodiment the dental irradiation device is adapted to display an image captured by the image sensing unit superimposed with a crosshair having a position and an area size indicator. The area size indicator is adapted to indicate an area in which the emitted light is suitable to harden a dental material. Thus the crosshair allows a user to position the dental irradiation device to a tooth and further to determine the area in which the light can cause a dental material to harden. The crosshair may computer generated and superimposed at the appropriate position with the image taken by the image sensing unit.

Further the dental irradiation device may be adapted to display an image captured by the image sensing unit superimposed with a level indicator for indicating a magnitude or level of an area illuminated by the first light emitting. Such magnitude may relate to the area of the light spot at the surface of the object in which the light spot has a predetermined intensity. The level indicator may be superimposed with the crosshair at the appropriate position and displayed to a user. The area of the light spot may by smaller or larger depending on the distance between the dental irradiation device and the illuminated area. Therefore the level indicator preferably comprises evaluation means for measuring the light intensity at different positions of an object. An area in which the intensity is sufficient to harden a dental material may be indicated by the level indicator, for example by a further circle and/or by a colored area (for example green for an area in which the intensity is sufficient and red in which it is not). Depending on the indicated level a user may then reposition the dental irradiation device, using for example the circle of the crosshair which may indicate an optimum area to be illuminated.

In one embodiment the dental irradiation device comprises a micro-radar for distance measuring. Radar measuring may be particularly advantageous for measuring the distance relative to transparent or translucent objects.

In one embodiment the dental irradiation device is adapted for bidirectional data transmission. The data to be transmitted comprise a barcode, acoustic signals (for example for voice control), position and distance data, movement control data, color information and further information data. In a particular embodiment the dental irradiation device is adapted to transmit a barcode, acoustic signals, position and distance data and movement control data to a computer. The computer may be configured to interpret the barcode, for example to identify a certain dental material from the barcode and to preselect certain parameter of the dental irradiation device, like a minimum time for hardening the dental material by the first light emitting unit, and/or a minimum intensity for hardening the dental material. The computer may further be adapted to interpret a sound (for example "start", "stop") received by the dental irradiation device to control the dental irradiation device. Further the computer may be adapted to interpret from one or more images taken a color, position, distance and/or movement of the device relative to an imaged object. The data connection between the dental irradiation device and the computer is preferably wireless.

In a further aspect the invention relates to a method of operating a dental irradiation device which comprises a first light emitting unit for emitting blue light adapted for light hardening of a dental material, a second light emitting unit and an image sensing unit, the second light emitting unit and the image sensing unit being adapted for cooperation with each other for simultaneous illumination and image capturing. The method comprises the steps of:

recognizing the distance between the device and an object; and one or both steps of:
automatically adjusting the light intensity of the first light emitting unit depending on the determined distance; and/or
automatically setting a time period and automatically switching off the first light emitting unit upon lapse of this time period depending on the determined distance.

In one embodiment the method further comprises the steps of:
automatically focusing to an object to be imaged by use of an autofocus camera;
using an output of the autofocus camera to determine the distance of the object focused.

In an alternative embodiment the method further comprises the steps of:
projecting a light spot to an object;
recognizing an image of the light spot; and
evaluating the size of the light spot and/or an area in which a predetermined minimum light intensity is recognized and based thereon determining the distance of the object.

The light spot of this embodiment is preferably projected by the first and/or second light emitting unit.

BRIEF DESCRIPTION OF THE FIGURES

FIG. 9b is a bottom view of the portion shown in FIG. 9a;

DETAILED DESCRIPTION OF THE INVENTION

Figure 1:
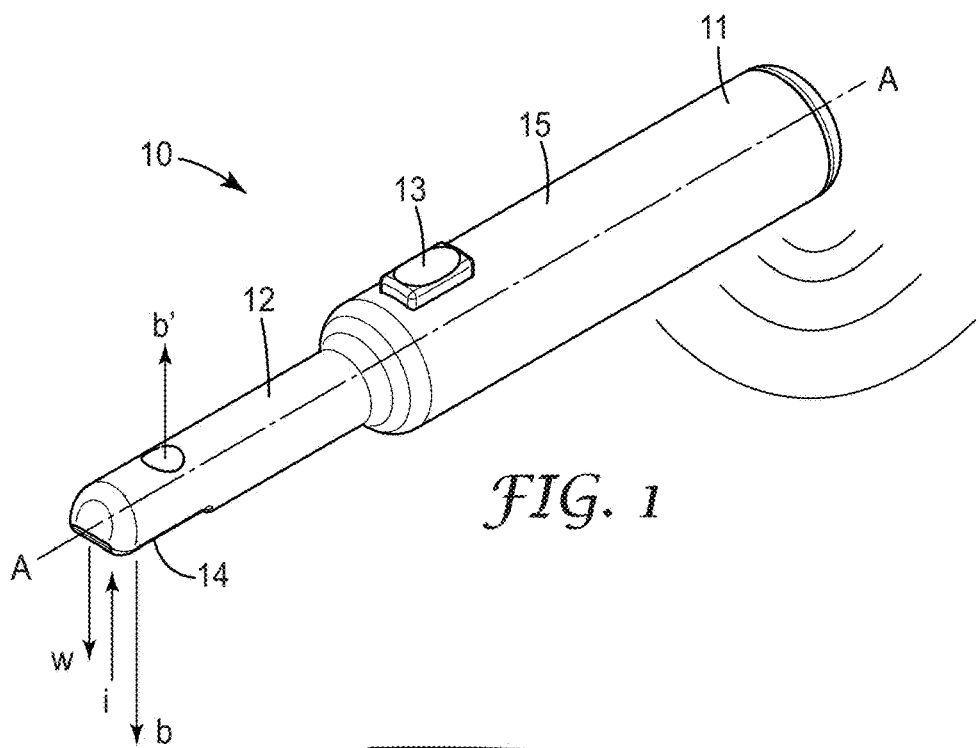
FIG. 1 is a perspective view of a dental irradiation device according to an embodiment of the invention.

FIG. 1 shows a dental irradiation device 10 comprising a body 11 and an intra-oral tip 12. The device 10 extends along a longitudinal axis A which in the example is generally straight, but may in another example be curved. The intra-oral tip 12 laterally to the longitudinal axis A has a reduced dimension relative to the body 11. This minimizes the space which is needed for positioning the intra-oral tip 12 in a patient's mouth, whereas the body 11 allows for accommodation of electronic components for operation of the device 10. The body 11 forms a handle 15 allowing a user to hold the device 10, for example during operation. The device 10 is generally adapted for emitting overall blue light and preferably for emitting white light. The device may be adapted for emitting blue light and simultaneously or alternatively white light. Further the device 10 is adapted for image capturing. Although not visible in detail in this Figure the device 10 has a first light emitting unit for emitting overall blue light, a second light emitting unit and an image sensing unit. Respective light outputs of the first and second light emitting unit are provided within a head portion 14 of the intra-oral tip 12. The head portion 14 is preferably arranged adjacent a free end of the device 10, and in particular is arranged adjacent a free end of the intra-oral tip 12 or forms the free end of the intra-oral tip 12. Further an image input of the image sensing unit is provided adjacent the head portion 14 of the intra-oral tip 12. For the purpose of this invention the light outputs and/or the image input may be generally formed by one or more optical interfaces of the device 10 allowing light to exit the device and/or for allowing light to enter into the device. Such an output/input may for example be formed directly by an electronic component, for example a light source, like a LED (light output), or a sensor like a CCD chip (image input). Further such an output/input may be formed by an additional optical unit for guiding light between the output/input and an electronic component as mentioned.

The head portion 14 of the intra-oral tip 12 of the device 10 preferably comprises the light outputs of the first and second light emitting units as well as the image input of the image sensing unit. The first light emitting unit may be configured and arranged in the device such that light therefrom can be emitted in a first direction which is indicated as "b". Optionally the first light emitting unit may be configured and arranged in the device such that light therefrom is emitted in an alternative first direction which is indicated as "b". Further the second light emitting unit may be configured and arranged in the device such that light therefrom is emitted in a second direction which is indicated as "w". The image sensing unit may be configured and arranged in the device such that light can enter the device (for example light reflected from an object) in a third direction which is indicated as "i". The first, second and third directions "b", "w", "i" may be oriented along generally the same dimension, or may be oriented within a maximum angular range of about 0 degrees to 30 degrees relative to each other.

The device 10 further has an actuator 13 for activating a function of the device. In the example the actuator 13 is a button for switching the first light emitting unit for blue light on or off. The device may have one or more further buttons, for example one button for switching the image sensing unit on and off. Switching the image sensor on or off may further cause the second light emitting unit to automatically switch on or off, respectively. A further button may be arranged on the device for manually switching the second light emitting unit on or off, for example independent from the image sensor. The device may further comprise a button for adjusting a duration for which at least the first light emitting unit for emitting blue light may operate for an adjusted time period before it switches off automatically after activation. The device may further comprise a button, two buttons or a slide for zooming in and/or out an image captured by the image sensor. Certain functions of the device may be further controlled via a computer as illustrated in FIG. 2 which is connectable to the device 10, for example via a wireless interface.

Figure 2:
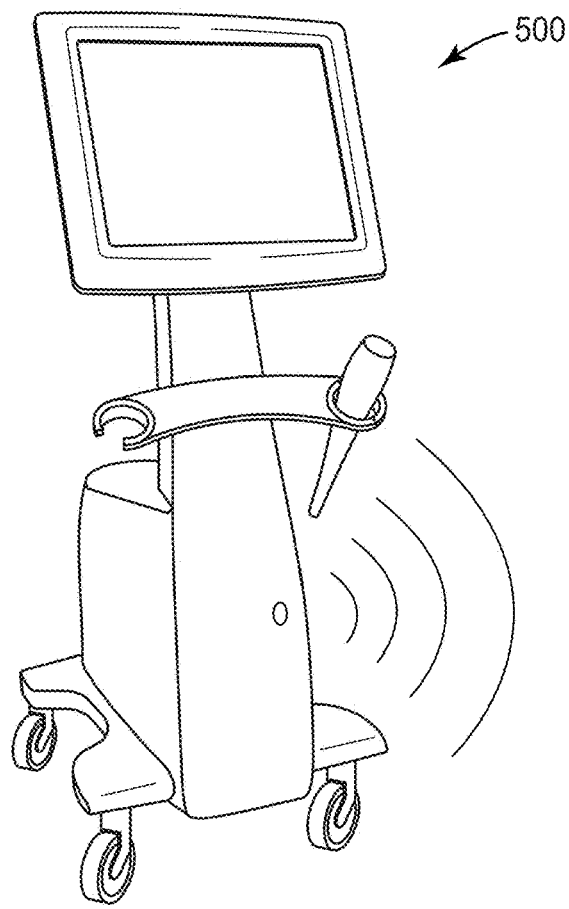
FIG. 2 is a perspective view of a computer forming part of a system according to an embodiment of the invention.

FIG. 2 shows a computer 500 which in the example is adapted to communicate via a wireless interface with a dental irradiation device of the invention. The person skilled in the art will recognize that the dental irradiation device and the computer may be adapted to communicate via a wireless and/or a wired connection. The dental irradiation device and the computer may in combination form a system which allows for example for hardening a dental material, transillumination of teeth, visualization of teeth, fluorescence measurement, and color matching.

Hardening

The system (computer 500 and a dental irradiation device of the invention) may be adapted such that for hardening dental material a hardening or curing time and/or the light intensity can be adjusted. The hardening time preferably corresponds to a time period over which the first light emitting unit is activated. The hardening time may for example be pre-adjustable or pre-selectable. Pushing (or otherwise actuating) the actuator of the dental irradiation device may trigger the first light emitting unit to be activated so that it emits blue light. The system may be adapted such that the first light emitting unit deactivates automatically upon the hardening time lapses. The system may be further adapted such that the hardening time can be pre-adjusted via the computer 500 or via the device, for example by a user input. In one example the system is configured such that the hardening time can be automatically determined by the computer dependent on a certain dental material which is entered in the computer, for example by selection from a database. Further the system may be configured for recognizing an encoding (for example a bar code) via the image sensing unit of the device. Such encoding may be received by the computer and used for determining the hardening time for example by retrieving the hardening time from a database dependent on the captured encoding.

The system may be further adapted such that the position of the device relative to the material to be hardened can be visualized. For example the system may be adapted to activate the image sensing unit for continuously capturing images and displaying them real time on the computer screen. Thus a user can position the device toward the dental material to be hardened and simultaneously monitor the position of the device relative to the material via the computer screen. During the positioning of the device the first light emitting unit may be inactivated, and only upon reaching the desired position may be activated, for example manually by the user. The system may be adapted to display a cross-hair for indicating the location toward which the blue light which can be emitted from the first light emitting unit is directed.

In an embodiment the device may have at least one laser pointer which points in the direction of the blue light which can be emitted from the first light emitting unit. The laser point may help the user appropriately position the device during the blue light is switched off. For example the laser pointer may be adapted such that it emits light in the same direction as the first light emitting units is adapted to emit blue light toward. The laser pointer may emit a narrow light beam for projecting a clear delimited point on a surface so that a user can precisely position the device by help of the laser point. The person skilled in the art will recognize that the laser light may be adapted such that it substantially does not interact with the dental material for hardening. The laser light might for example be outside the wavelength of blue light, for example may have a wavelength of green or red light. Further the device may have two spaced laser pointers which point at an angle relative to each other such that the laser beams intersect at a predetermined distance from the device. The position of the intersection preferably corresponds to an optimum distance of the device relative to the material to be hardened so that upon activation the first light emitting unit the device is also positioned at the desired distance to the material. In that regard an optimum distance may be a distance at which the dental material is irradiated at a sufficient intensity to harden and at a sufficient distance to avoid overheating of the dental material.

Further the system may be adapted such that during hardening of the dental material the visualization may be activated or deactivated. For example the system may be adapted such that activating the first light emitting unit automatically causes the image sensor to deactivate. Thus the image sensor may not need to be adapted to capture images under (relatively intense) blue light so that costs may be minimized. The system may further be adapted such that the first light emitting unit is frequently interrupted for capturing an image during the interruption only. Thus the system may allow for monitoring the position of the device relative to the dental material during hardening but without the need to capture images under blue light.

The system may however further be adapted such that the image sensing unit can capture images under blue light conditions. Thus the system may allow for observing the dental material and its position while it is hardened. Accordingly the system thus may provide for an "electronic light shield", which helps user to avoid directly viewing into the relative intense blue light but rather provides the user with an image on a screen at acceptable light intensity. This may help minimizing risks for the user's eyes as they may result from viewing directly into relative intense blue light or a spot irradiated by blue light.

Visualization

The system may be adapted to visualize of an area via the image sensing unit, for example to display an image sensed by the device on a screen. The visualization function may generally comprise an illumination of the area by the second light emitting unit. The illumination may be activatable and deactivable, for example by a user. Further the second light emitting unit is preferably adapted to provide light which is appropriate for the image sensing unit to capture an image from an object illuminated by that light. In the example the second light emitting unit is adapted to emit white light. The system may be adapted to capture images continuously, to stream the image (for example via wireless data connection) to the computer and to display the images real time on the computer screen. Further the system may be adapted to pause the streaming or to take a photograph. Thus the computer may be adapted to display an image of a particular detail of a captured area. Further the computer may be adapted to zoom into an image displayed, and/or may allow for virtually drawing or marking a particular detail in an image. Thus a user, for example a dental practitioner, may be enabled to highlight certain details on an image, for example to explain a patient a certain clinical situation or planned treatment regarding the patient's teeth.

Measuring of Fluorescence

The system may be configured to measure fluorescence of a tooth by use of the image sensor and the second light emitting unit (or an additional further light emitting unit) providing for the appropriate illumination. In such a system the computer may have software for interpretation of the captured image and for determining the fluorescence therefrom. The software may further allow for controlling the second light emitting unit (or the additional further light emitting unit) for emitting light at particular wavelengths and/or intensities.

Color Matching

The system may be adapted to perform a so-called color matching. The color matching may comprise the capturing of an image via the image sensing unit and displaying the image on the computer screen relative to a reference color. A user may thus be enabled to compare the reference color and the color(s) of the image with each other. This may for example be helpful for a user to select an appropriately colored dental material intended to restore a tooth from which the image was taken. The system may further be adapted to evaluate one or more colors of the image and to display values of such the colors, for example values in the L*a*b color system or values relating to the VITA™ color system (for example A2, A3, B1 etc.). A user may thus be enabled to select a dental material at a desired color based on such color values. Further the system may be adapted for automatically determining one or more appropriately colored dental materials and for suggesting one or more determined dental materials to a user.

Trans-Illumination

The system may further be adapted for activation of the second light emitting unit, for example for activation of only the second light emitting unit. Thus the device of the invention may be used for trans-illuminating a tooth by white light, for example for diagnosis of the tooth for the presence of caries or the approximate boundaries of a present tooth filling. The skilled person will recognize further applications which are enable by the device and system of the invention.

Figure 3:
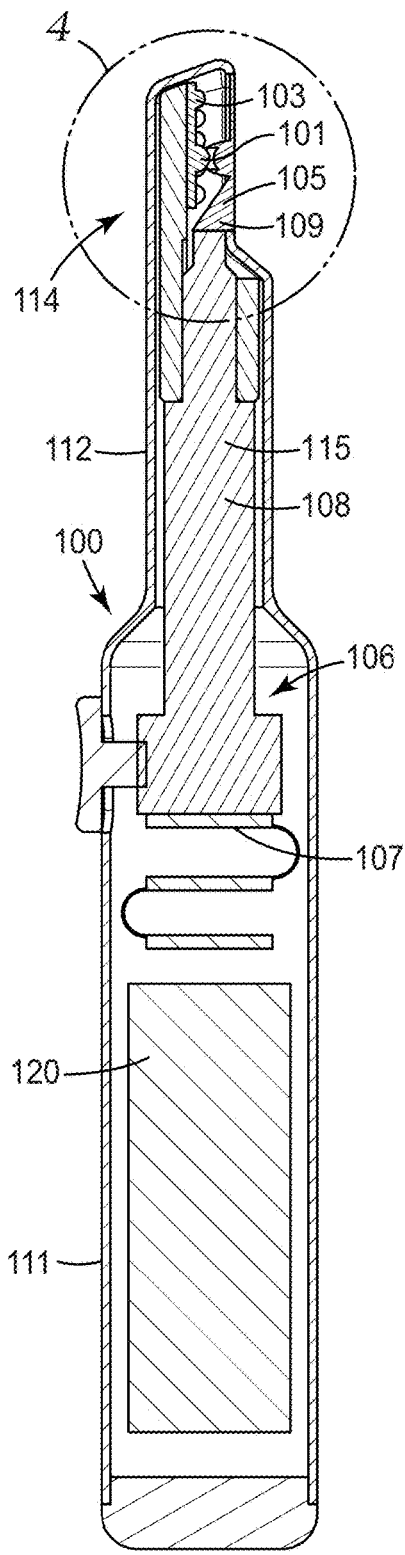
FIG. 3 is a cross-sectional side view of a dental irradiation device according to one embodiment of the invention.

FIG. 3 shows a dental irradiation device 100 which has the general features of the example shown in FIG. 1. The device 100 has a body 111, and an intra-oral tip 112. A head portion 114 (shown enlarged in FIG. 4) of the intra-oral tip 112 comprises a first light output 101. The first light output 101 is part of a first light emitting unit 102 which is adapted for emitting overall blue light. In the example the first light emitting unit 102 comprises a light source which is accommodated with the head portion 114. The light source is a single high power LED in this example. A preferred light source for the first light emitting unit 102 is formed by one single high power LED providing light at a peak wavelength within a range of about 444 nm to about 452 nm. Although a single LED is preferred the skilled person will recognize that two or more LEDs of the same type can be used without departing from the present invention. However the person skilled in the art will recognize that a plurality of LEDs might be used in the alternative. The head portion 114 further comprises a plurality of second light outputs 103 which are part of a second light emitting unit 104. The second light emitting unit 104 comprises a plurality of light sources which provide white light. In the example the light sources are white LEDs each forming one of the second light outputs 103. The second light outputs 103 (and thus the white LEDs) are arranged such that they surround an image input 105 which in the example is formed by an optical prism 109. The prism 109 may form part of a transparent screen which closes a window in the head portion 114 of the device 100 and though which the first and second light outputs 101, 103 can emit light. The image input 105 is part of an image sensing unit 106 which comprises an image sensor 107 (for example a CCD chip), an optical unit 108 and the prism 109. In the image sensing unit 106 the optical unit 108 is adapted to convey an image from the prism 109 toward the image sensor 107. The optical unit 108 may comprise one or more optical lenses, apertures and/or light guides. Further the optical unit 108 may provide an optically enlarged image at the image sensor 107 relative to the image provided via the prism 109. Thus a relatively large image sensor 107 may be used, for example an image sensor capable of capturing an image at relatively many image pixels. This preferably provides for an image at a relatively high resolution.

The device 100 in the example has a battery 120 which provides a wireless power supply for the device 100. The battery 120 is a rechargeable battery which may be recharged in a contact or contactless manner. The person skilled in the art will recognize that the device 100 may further be supplied by a wired connection, although a wireless operation of the device is preferred. Further the device 100 may have electronic circuitry which allows for controlling at least some of the device's functions. The electronic circuitry preferably comprises a data interface for communication with a computer (for example one as shown in FIG. 2). Further the electronic circuitry preferably comprises safety functions, for example to avoid overheating of the device during operation, or for controlling battery charging and discharging.

Figure 4:
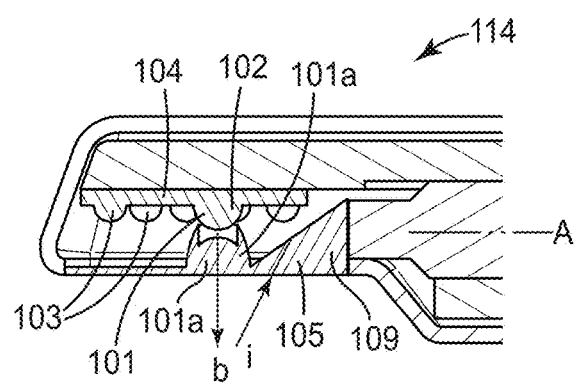
FIG. 4 is a cross-sectional partial side view of a portion of the device shown in FIG. 3.
Figure 5:
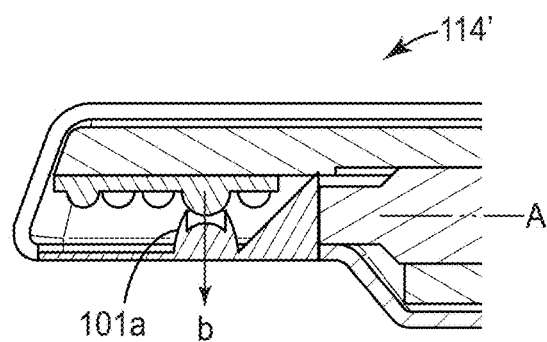
FIG. 5 is a cross-sectional partial side view of a portion of a device according to a further embodiment of the invention.
Figure 6:
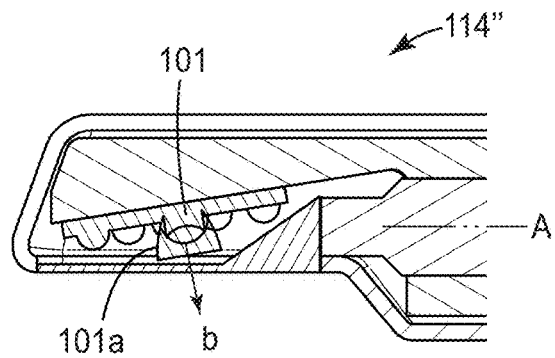
FIG. 6 is a cross-sectional partial side view of a portion of a device according to still a further embodiment of the invention.

FIGS. 4, 5 and 6 show different embodiments of a head portion 114/114'/114" as they may be used with the device 100 illustrated in FIG. 3. Generally in all embodiments shown in FIGS. 4 to 6 the first light output 101 comprises a TIR lens™ (Total Internal Reflection lens) 101a for collimating the blue light emitted from the LED of the first light emitting unit. Thus the TIR lens™ provides for the blue light to be emitted as a light beam of generally parallel extending light. As an alternative of a TIR lens™ a plano-convex lens may be used. In the embodiment shown in FIG. 4 the prism 109 has a triangular profile with the angles of the triangle being arranged such that a spot illuminated or illuminatable by the blue light can also be captured by the image sensing unit at the same position of the device relative to the spot. In other words the first light emitting unit and the image sensing unit are adapted and arranged such that the third direction "i" (see Figure) and the first direction "b" (see Figure) intersect at a predetermined distance relative to the head portion 114. The profile of the prism 109 has preferably a non-equal sided triangular shape. This causes a light ray to be deflected by the prism at an angle other than 90 degrees. In FIG. 6 the first light emitting unit and the image sensing unit are also adapted and arranged such that the third direction "i" (see Figure) and the first direction "b" (see Figure) intersect at a predetermined distance relative to the head portion 114. However in this embodiment the first light output 101 is inclined relative to the arrangement shown in FIGS. 4 and 5. In the example of FIG. 6 the prism 109 may have an equal or non-equal triangular shape. FIG. 5 shows an example in which the first light emitting unit and the image sensing unit are adapted and arranged such that the third direction "i" (see Figure) and the first direction "b" (see Figure) are generally parallel. Accordingly in the embodiments of FIGS. 4 and 5 the first light emitting unit is adapted for emitting blue light in a direction "b" which is oriented generally perpendicular to the longitudinal axis A of the device. In the embodiments of FIG. 4 and (optionally) FIG. 6 the image sensing unit is adapted to capture an image from a direction "i" which is non-perpendicular and non-parallel to the longitudinal axis A, whereas in the embodiments of FIG. 5 and (optionally) FIG. 6 the image sensing unit is adapted to capture an image from a direction "i" which is generally perpendicular to the longitudinal axis A.

Figure 7:
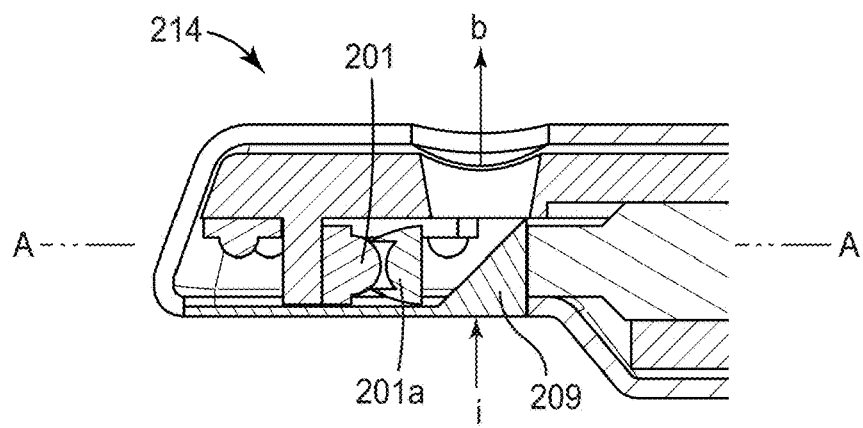
FIG. 7 is a cross-sectional partial side view of a portion of a device according to another embodiment of the invention.

FIG. 7 shows a head portion 214 of a dental irradiation device (not shown entirely) in which the first light output 201 (with TIR lens™ 201a) is arranged to emit light generally parallel to the longitudinal axis A. The prism 209 in this example is adapted and arranged to deflect light for capturing an image by about 90 degrees by internal reflection and to deflect the blue light emitted from the first light output 201 by about 90 degrees by outside reflection. Accordingly the image sensing unit is adapted for capturing an image from a direction "i", the first light emitting unit is adapted to emit light in a direction "b" with the directions "i" and "b" being oriented in the same direction. This means that the device can be used for capturing an image of a spot in a first position of the device relative to the spot and in a different second position for irradiating the same spot. The first and second positions in the example differ by a rotation of the device about the longitudinal axis A by about 180 degrees.

Figure 8:
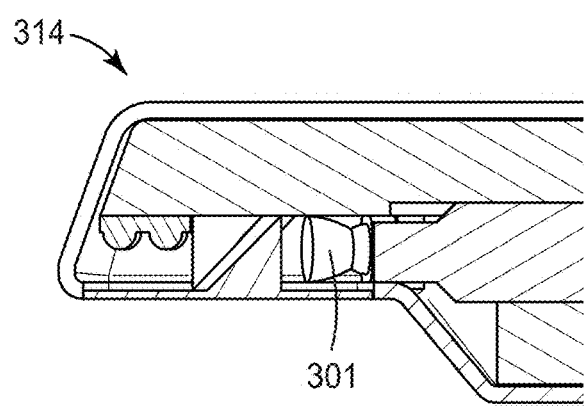
FIG. 8 is a cross-sectional partial side view of a portion of a device according to a further embodiment of the invention.
Figure 8A:
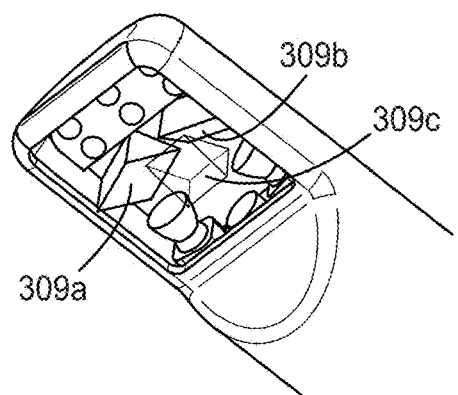
FIG. 8*a* is a perspective bottom view of a detail of the device shown in FIG. 8.

FIG. 8 shows a further embodiment in which two prisms 309a, 309b and a further prism 309c (see FIG. 8a) are arranged and adapted to deflect light for capturing an image by about 90 degrees by internal reflection and to deflect the blue light emitted from the first light output 201 by about 90 degrees by outside reflection. However in contrast to the embodiment of FIG. 7 the prisms 309a, 309b, 309c are arranged such that the image sensing unit is adapted for capturing an image from a direction "i", the first light emitting unit is adapted to emit light in a direction "b" with the directions "i" and "b" being oriented in opposite directions. Hence the head portion 314 allows for a dental irradiation device with which the head portion 314 is used for capturing an image of a spot and for irradiation of the same spot at the same position of the device relative to the spot.

Figure 9:
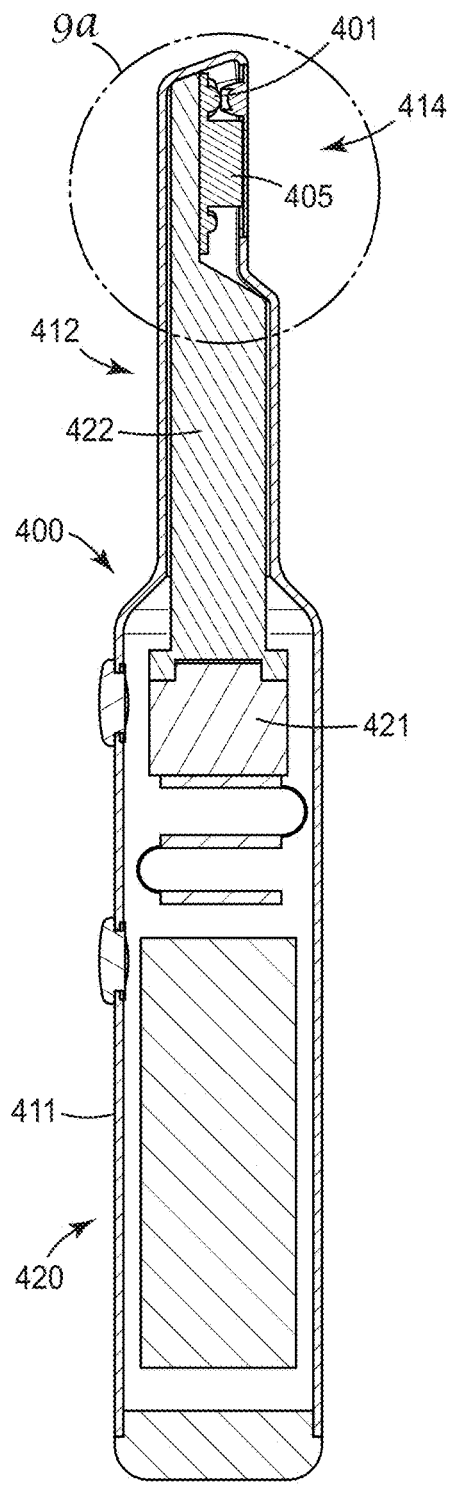
FIG. 9 is a cross-sectional side view of a dental irradiation device according to a further embodiment of the invention.
Figure 9A:
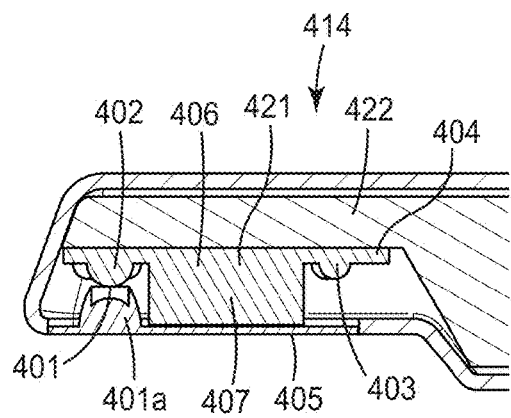
FIG. 9a is a cross-sectional partial side view of a portion of the device shown in FIG. 9.
Figure 9B:
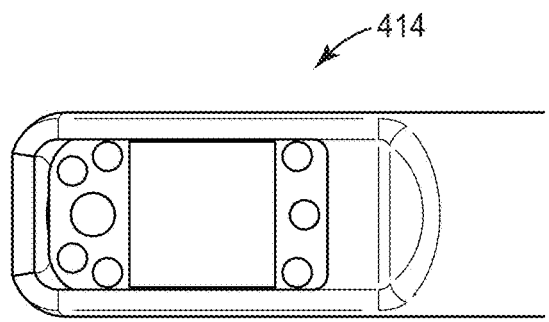

FIG. 9 shows a further embodiment of a dental irradiation device 400 according to the invention. The dental irradiation device 400 has the general features of the example shown in FIG. 1. The device 400 has a body 411 and an intra-oral tip 412. A head portion 414 (shown enlarged in FIGS. 9a and 9c) of the intra-oral tip 412 comprises a first light output 401. In the example the first light output 101 is part of a first light emitting unit 402 which is adapted for emitting overall blue light. As mentioned above the blue light is provided by a single high power LED, but a plurality of LEDs may be used likewise. The head portion 414 further comprises a plurality of second light outputs 403 which are part of a second light emitting unit 404. The second light emitting unit 404 comprises a plurality of white LEDs each being assigned to one of the second light outputs 403. The second light outputs 403 (and the assigned white LEDs) are arranged around an image input 405 which in the example is formed by an image sensor 407. The image input 405 is part of an image sensing unit 406 which comprises image sensor 407 (for example a CCD chip). The first light output 401, the second light outputs 403 and the corresponding light sources may be arranged on one common circuit board 412 with the image sensor 407. The common circuit board 412 is preferably arranged on a heat sink 422 for dissipating heat generated by the light sources and the image sensor during operation of the device.

The image sensing unit 406 may comprise electronic circuitry and a housing for the image sensor 407 but may not have an optical unit comprising a plurality of lenses as in the example of FIG. 3. The image sensing unit 406 may however comprise a lens, for example a zoom lens, which is arranged adjacent the image sensor 407. A fixed zoom lens may be formed by one or more magnification lenses, whereas a variable zoom lens may comprise at least two, preferably three or more lenses of which at least one is variably positionable relative to the other lenses. The lens or lenses may for example be positioned via a motor which can be controlled by the device. The device may further or alternatively have a digital zoom.

In this example the first and second light emitting units and the image sensing unit are preferably entirely accommodated in the head portion 414.

The device 400 in the example further has a battery 420 for powering the device 400 as mentioned in the example of FIG. 3. Further the device 400 may have electronic circuitry 421 which allows for controlling at least some of the device's functions. The electronic circuitry 421 preferably comprises a data interface for communication with a computer (for example one as shown in FIG. 2).

Figure 10:
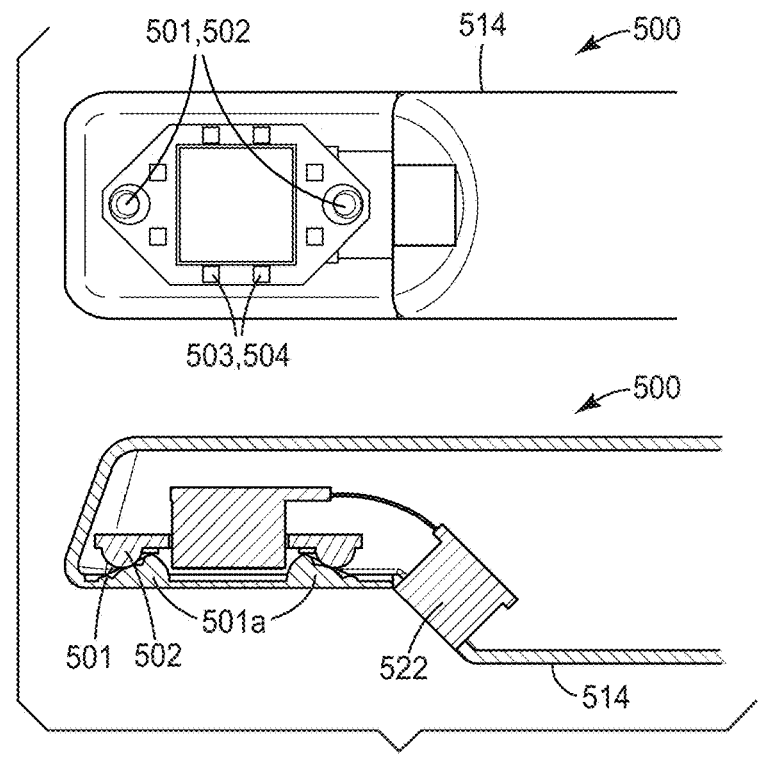
FIG. 10 is a bottom and side view of a dental irradiation device according to an embodiment of the invention.

FIG. 10 shows a head portion 514 of a dental irradiation device 500. The dental irradiation device 500 comprises within the head portion 514 a first light emitting unit 502 for emitting blue light and a second light emitting unit 504 for emitting white light. The first light emitting unit 502 has two first light outputs 501. Each of the light outputs 501 has preferably a single high power LED. Further each of the LEDs is assigned a collimating lens 501*a* for converting the light emitted by an LED into a generally parallel light beam. The lenses are preferably arranged such that they guide the light beams toward a predetermined location outside the head portion 514. Hence the two light beams cross and superimpose at that predetermined location in operation of the dental irradiation device 500. Although in this example two high power LEDs are used for maximizing the light intensity the skilled person will recognize that the same device may be implemented with only one or more than two high power LEDs.

The second light emitting unit 504 has plurality of second light outputs 503 each comprising a white LED. Further the dental irradiation device 500 comprises an image sensing unit 506 arranged within the head portion 514. In the example the image sensing unit 506 comprises an autofocus camera. The autofocus is preferably based on an autofocus mechanism which is adapted to physically move one or more lenses relative to a camera circuit (CCD or CMOS circuit). The autofocus mechanism has a motor (or actuator) for moving the lens(s) and the camera circuit relative to each other. In a preferred embodiment such motor is based on a wire made of a shape-memory alloy. The wire is connectable to electric power by which the wire can be heated. The wire is adapted such that it contracts in length if heated, and the material (for example nickel titanium) of the wire is selected such that its elastic modulus is higher if heated and lower if not heated. The autofocus mechanism further comprises a spring for resetting the wire in length if not heated. The spring is configured such that its force is sufficient for stretching the non-heated wire due to the wire's lower elastic modulus at the non-heated stage, and further such that it allows contraction of the heated wire against the spring force. Thus the length of the wire can be controlled by the power used to heat the wire, and accordingly the focus of the camera is adjustable by controlling the power applied to the wire. The camera therefore is preferably connected to an electronic controller which is adapted to control the power in a predetermined relationship to the position of the focus.

In the example such wire is mechanically arranged for positioning the lens(es) and the camera circuit relative to each other. And the controller is connected to the wire to control such positioning. The skilled person will recognize that in another example the autofocus mechanism may be based on a piezo-electric motor (for example a piezo-electric stepper motor) for positioning the lens(es) and the camera circuit relative to each other.

The image sensing unit 506 further is adapted to automatically focus to an object to be imaged by the image sensing unit 506. The skilled person will recognize various technical solutions for automatic focusing, one of which being based on contrast detection. In contrast detection contrast is measured by a sensor array through the lens. The intensity difference detected by adjacent pixels of the sensor array has a maximum at the correct focus, so that the correct focus can be reached by adjusting the lens(es)/camera circuit position toward the maximum contrast.

Preferably the dental irradiation device 500 is further adapted to recognize the distance of an object focused by the camera. The distance of the object can be determined, for example from the power used for heating the wire in an autofocus based on shape-memory alloy, because a certain power applied to the wire results in a determined corresponding position of the camera focus. Further the dental irradiation device 500 is preferably adapted to automatically adjust the light intensity of the first light emitting unit 502 depending on the distance of the imaged object. For example if the object is located closer to the head portion 514 (and thus to the image sensing unit 506) the first light emitting unit 502 may be controlled to emit light at a lower intensity compared to an object being located further remote from the head portion 514. Thus the dental irradiation device 500 is preferably adapted to radiate an object, for example a dental material, at generally uniform intensity independent from the distance between the head portion 514 and the object. In particular the dental irradiation device 500 is preferably adapted to compensate a variation of the distance between the head portion 514 and an object by controlling the intensity of the emitted light toward a uniform level at the position of the object.

In the dental irradiation device 500 the second light emitting unit 504 and the image sensing unit 506 are adapted for cooperation with each other for simultaneous illumination and image capturing.

The dental irradiation device 500 further has an additional color sensor 522. The color sensor 522 may comprise a further CCD or CMOS camera circuit. Further the color sensor 522 may comprise a plurality of light filters assigned to individual intensity sensors of the CCD or CMOS circuit. The color sensor 522 may comprises more than three different color filters. In contrast to a standard RGB camera based on three different color filters for measuring three different colors, the color sensor 522 thus allows measuring of more than three colors. In a preferred embodiment the color sensor 522 is configured for measuring at least eight, preferably at least fifteen different colors. Therefore the color sensor may comprise at least eight or at least fifteen, thirty or even sixty different color filters. Each of the color filters may be adapted to transmit light within a certain wavelength spectrum and block light outside the specified wavelength spectrum. Such filters are also referred to as "bandpass filters", and accordingly the mentioned wavelength spectrum is further referred to as "passband". Further each passband typically has a certain "bandpath width", which characterizes the size of the spectrum at which the filter is transmissive. Each of the color filters may have a passband width within a range of 5 nm (nanometers) to 40 nm, more preferably within a range of 5 nm to 25 nm, most preferably within a range of 5 nm to 10 nm. Bandpass filters are available in many different configurations, including many different bandpass widths and spectra. The skilled person will recognize that a color sensor can likewise be provided by use of so-called band-stop filters, although bandpass filters are preferred herein.

The color sensor 522 is preferably configured measure a tooth color. Further the dental irradiation device 500 is preferably adapted for image capturing (via the image sensing unit 506) and for color measuring (via the color sensor 522) simultaneously. Therefore the device allows imaging of a tooth shape in combination with relatively precisely measuring the color of the imaged tooth.

Figure 11:
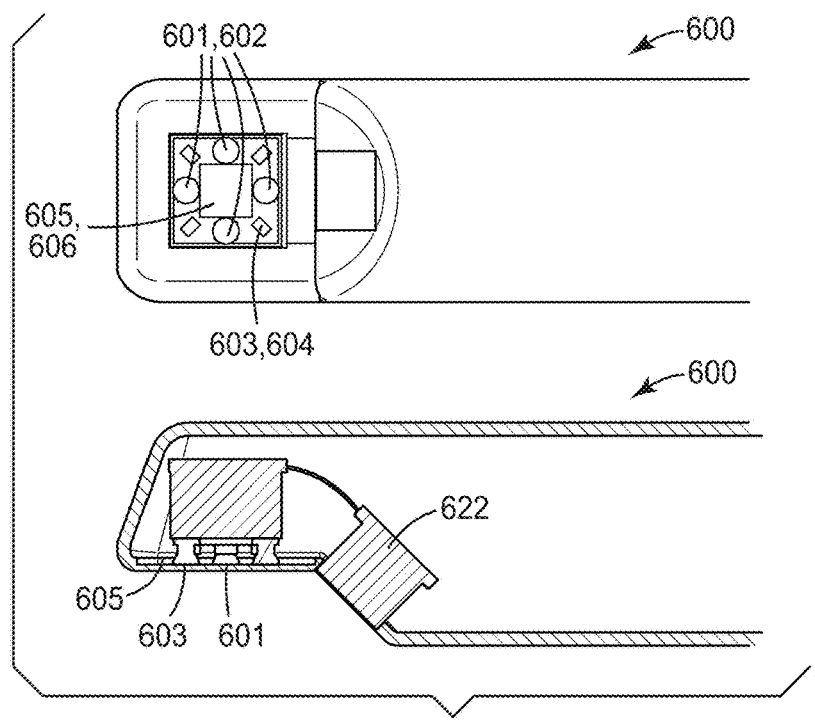
FIG. 11 is a bottom and side view of a dental irradiation device according to a further embodiment of the invention.

FIG. 11 shows a head portion 614 of a dental irradiation device 600. The dental irradiation device 600 comprises within the head portion 614 a first light emitting unit 602 for emitting blue light and a second light emitting unit 604 for emitting white light. The first light emitting unit 602 has four first light outputs 601. Each of the light outputs 601 has preferably a single high power LED. Further each of the LEDs may be assigned a collimating lens to guide the light beams of all four first light outputs 601 toward a predetermined location outside the head portion 614.

The second light emitting unit 604 has four second light outputs 603 each comprising a white LED. Further the dental irradiation device 600 comprises an image sensing unit 606 arranged within the head portion 614. The image sensing unit 606 comprises an autofocus camera including a function for distance measuring as described in the example of FIG. 10.

In the dental irradiation device 600 the second light emitting unit 604 and the image sensing unit 606 are adapted for cooperation with each other for simultaneous illumination and image capturing. The dental irradiation device 600 further has an additional color sensor 622 as described in the example of FIG. 10.

In the example shown an image input 605 is offset behind a plane in which the first and second light outputs 601, 603 are arranged. In particular regarding a direction in which the first and second light outputs 601, 603 emit light the image input 605 is arranged offset behind the first and second light outputs 601, 603.

Figure 12:
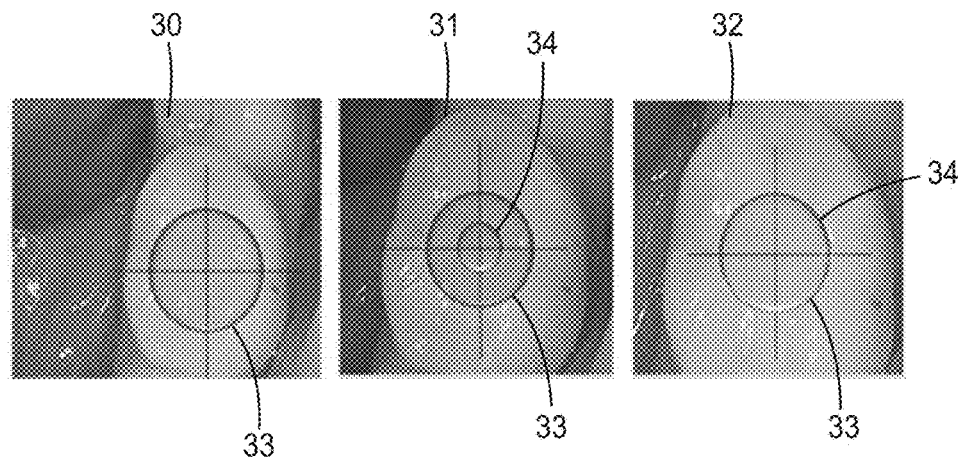
FIG. 12 illustrates displays of images as they may be captured by a dental irradiation device according to the invention.

FIG. 12 illustrates three different displays 30, 31, 32 of images as they may be captured by an image sensing unit according to the invention. Further the images of the example are obtained from a dental irradiation device which is equipped with a distance control means. As disclosed herein a distance control means may comprise at least two laser pointers the laser beams of which intersect at a predetermined distance outside a head portion of the dental irradiation device. However in the example the distance control means comprises means for evaluating the size and/or the intensity of light impinging an object imaged by the image sensing unit of the dental irradiation device. Preferably the light impinging on the object is emitted by the first light emitting unit (for example one having a blue LED) of the same dental irradiation device. Images 30, 31, 32 each illustrate a crosshair 33. The crosshair 33 has perpendicular crossing lines for indicating a center point of the light emitted from the dental irradiation device, and further the crosshair 33 has a circle origined in the center point and sized to indicate an area in which the emitted light may be used to harden a dental material. Thus the crosshair 33 allows a user to position the dental irradiation device relatively precisely to a tooth in a patient's mouth. The crosshair 33 is computer generated, superimposed at the appropriate position with the image taken by the image sensing unit, and displayed (for example on a computer screen) to a user of the dental irradiation device. Further the distance control means comprises a level indicator 34 (see image 31, 32) for indicating a magnitude of the light impinging on the object. Such magnitude may relate to the area of the light spot at the surface of the object in which the light spot has a predetermined intensity, for example one sufficient to harden a dental material. As shown in image 31 the level indicator is preferably superimposed with the crosshair 33 at the appropriate position and displayed to a user. In image 30 the level indicator is not visible because the dental irradiation device may be positioned at an out of range distance from the object. In this case the area within the circle of the crosshair 33 may be colored, for example in red, to indicate the user that the dental irradiation device is positioned out of range relative to the object imaged. The skilled person will recognize that the user may be informed about the out of range position otherwise, for example by a message or a separate indicator. In image 31 the level indicator 34 is present, however, is smaller than the circle of the crosshair 33. This indicates a user that the dental irradiation device is positioned too close to the object and therefore should be moved away until the size of the level indicator generally corresponds to the size of the crosshair's circle. To provide a better visibility the area surrounded by the level indicator may be filled by a color which is different from the color of the area surrounded by the crosshair's circle. For example the area within the level indicator may be colored green, whereas the area between the level indicator and the circle may be colored red (so that a green spot surrounded by a red ring is displayed). Thus a user may quickly determine that the dental irradiation device should be repositioned (in the example farther away from the object). In the image 32 the dental irradiation device is appropriately positioned relative to the object so that the level indicator and the crosshair coincide. To distinguish this situation from the situation of image 30 the area inside the crosshair's circle in image 32 may be colored in a different color than the same area in image 30, in the example green. Again the appropriate positioning may be indicated otherwise, for example by a message or separate indicator.

The display of the level indicator 34 may be based on an image recognition of the light spot on the object, for example from evaluating the size of the light spot and/or from evaluating an area in which a predetermined minimum light intensity is recognized (for example from evaluating the brightness of the spot at different points). Further the display of the level indicator 34 may be based on distance measuring by any appropriate means, for example by distance measuring via an autofocus camera, laser triangulation or radar measuring.

In one example (not shown) the dental irradiation device may comprise a micro-radar for distance measuring. Such a micro-radar may operate at about 122.5 GHz ISM-band and may thus be adapted to determine the distance of an object relative to the radar. Radar measuring may be particularly advantageous for measuring the distance relative to transparent or translucent objects, for example particularly incisal teeth, which sometimes may be difficult to measure optically. An appropriate radar sensor was developed by the SUCCESS consortium (Silicon-based Ultra compact Cost-efficient System design) funded by the European Commission.

Figure 13:
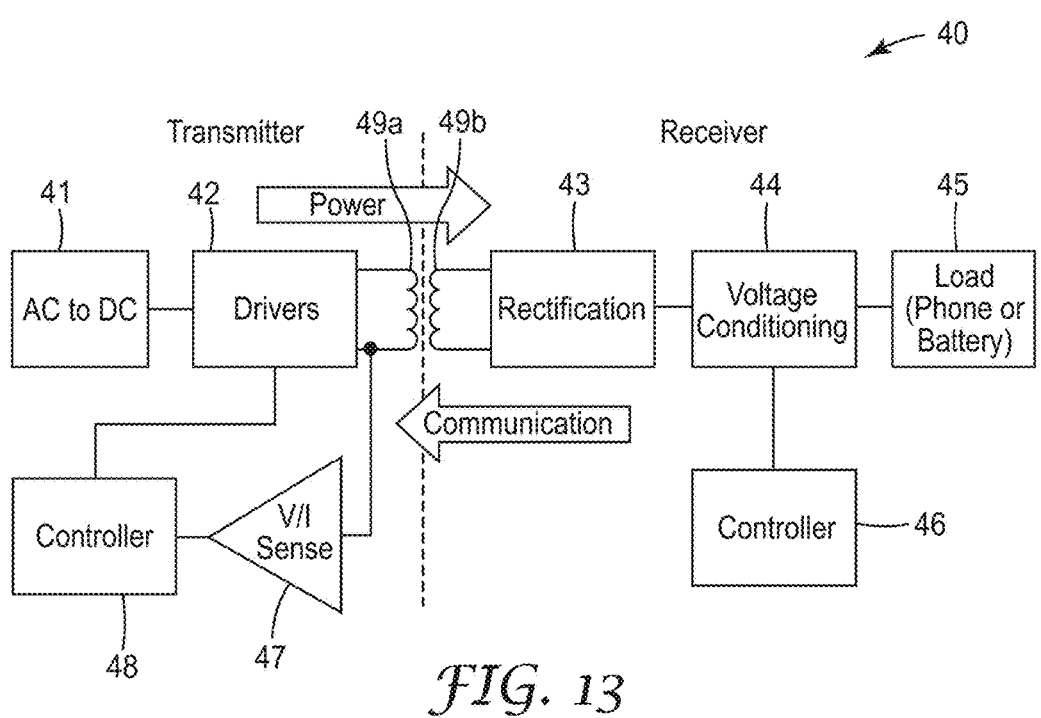
FIG. 13 is a schematic circuit diagram of a wireless charging system as it may be used for the dental irradiation device of the invention.

FIG. 13 shows a schematic circuit diagram of a wireless charging system 40 as it may be used for the dental irradiation device of the invention and particularly in combination with each of the examples described herein. The wireless charging system 40 is based on the "Qi" Wireless Power Standard. Such standard allows relative efficient wireless charging and further enables charging of the dental irradiation device by use of a standard charging device. Such standard charging device may be adapted to cooperate with a variety of different portable devices including smart phones, tooth brushes and other devices. Hence a user of the dental irradiation device of the invention may not need a separate customized charging device. In the diagram the following components are provided (in a clockwise order): AC to DC converter 41, drivers 42, rectification 43, voltage conditioning, battery of portable device or dental irradiation device 45, controller 46, V/I sense, controller 48. The components 43, 44, 45 and 46 are preferably comprised within the dental irradiation device 45, and the components 41, 42, 47, 48 are preferably part of the charging device. Further the charging device as well as the dental irradiation device have coils 49a, 49b respectively. The coils 49a, 49 are adapted to inductively cooperate with each other for power transmission, for example when positioned sufficiently close to each other.

The invention claimed is:

1. A dental irradiation device comprising a first light emitting unit for emitting blue light for light hardening of a dental material, a second light emitting unit and an image sensing unit, the second light emitting unit and the image sensing unit being cooperative with each other for simultaneous illumination and image capturing, wherein the dental irradiation device causes to be displayed an image captured by the image sensing unit superimposed with a crosshair having a position and an area size indicator, wherein the area size indicator indicates an area in which the emitted light is suitable to harden the dental material, wherein the crosshair is computer generated and superimposed at the appropriate position on the image taken by the image sensing unit, and wherein the dental irradiation device causes to be displayed the image captured by the image sensing unit superimposed with a level indicator superimposed with the crosshair for indicating intensity at which the area illuminated by the first light emitting unit and wherein the level indicator is computer generated.

2. The dental irradiation device of claim 1, wherein the first light emitting unit is arranged in the dental irradiation device for irradiation of a reference area in the same reference position of the device.

3. The dental irradiation device of claim 2, wherein the second light emitting unit is arranged in the dental irradiation device for illumination of the reference area in the same reference position of the device.

4. The dental irradiation device of claim 1, wherein the second light emitting unit emits white light.

5. The dental irradiation device of claim 1, wherein the first light emitting unit has a first light output, the second light emitting unit has a second light output, and the image sensing unit has an image input, wherein the first and second light output and the image input are arranged in the device adjacent each other.

6. The dental irradiation device of claim 5, wherein the image sensing unit comprises an image sensor and an optical unit for guiding light between the image sensor and the image input.

7. The dental irradiation device of claim 1, wherein each of the first and second light emitting unit comprises one or more light emitting diodes (LEDs), and wherein the image sensing unit comprises a charge-coupled device (CCD) or complementary metal-oxide-semiconductor (CMOS).

8. The dental irradiation device of claim 7, wherein the light emitting diodes (LEDs), and the image sensing unit are provided on a chip-on-board (COB) module.

9. The dental irradiation device of claim 1, further comprising a collimation optic for collimating light emitted from the first and/or second light emitting unit.

10. The dental irradiation device of claim 1, further comprising a fixed or variable optical zoom lens.

11. The dental irradiation device of claim 1, further comprising a light wave converter for the first light emitting unit for providing light at a light temperature of about 5000 K or greater.

12. The dental irradiation device of claim 1, further comprising a wireless data interface for transmitting image data obtained from the image sensing unit.

13. The dental irradiation device of claim 12 further including a handle body and an intra-oral tip, wherein the intra-oral tip and the handle body are rotatably and detachably interconnected with each other.

14. The dental irradiation device of claim 1, further comprising a color sensor in addition to the image sensing unit.

15. A dental irradiation system, comprising the dental irradiation device of claim 1, and a computer to receive image data from the dental irradiation device and to display an image based on the image data.

* * * * *

UNITED STATES PATENT AND TRADEMARK OFFICE
CERTIFICATE OF CORRECTION

PATENT NO. : 10,231,810 B2
APPLICATION NO. : 14/427699
DATED : March 19, 2019
INVENTOR(S) : Jens Gramann Page 1 of 2

It is certified that error appears in the above-identified patent and that said Letters Patent is hereby corrected as shown below:

On the Title Page

Column 1
(Inventors), Line 2, delete "Stefan K. Welke" and insert -- Stefan Welker --, therefor.

Column 1
(Inventors), Line 2, delete "Seefeld" and insert -- Geltendorf --, therefor.

Column 1
(Inventors), Line 3, delete "Seefeld" and insert -- Gauting --, therefor.

Column 1
(Inventors), Line 4, delete "Seefeld" and insert -- Gauting --, therefor.

Column 1
(Inventors), Line 5, delete "Seefeld" and insert -- Germering --, therefor.

Column 1
(Inventors), Line 6, delete "Seefeld" and insert -- Kaufbeuren --, therefor.

Column 1
(Inventors), Line 7, delete "Seefeld" and insert -- Landsberg am Lech --, therefor.

Column 1
(Inventors), Line 8, delete "Seefeld" and insert -- Eichenau --, therefor.

In the Specification

Column 6
Line 64, delete "and or" and insert -- and/or --, therefor.

Signed and Sealed this
Twenty-ninth Day of October, 2019

Andrei Iancu
*Director of the United States Patent and Trademark Office*

Column 7
Line 38, delete "may by" and insert -- may be --, therefor.

Column 11
Line 67, delete "deactivable," and insert -- deactivatable, --, therefor.

Column 14
Line 49, before "prisms" insert -- 30 --.

Column 16
Line 1, delete "lens(s)" and insert -- lens(es) --, therefor.

Column 17
Line 17, delete ""bandpath width"" and insert -- "bandpass width" --, therefor.

Column 18
Line 15, delete "origined" and insert -- originated --, therefor.